United States Patent [19]

Coope et al.

[11] Patent Number: 5,410,076

[45] Date of Patent: Apr. 25, 1995

[54] PROCESS FOR THE PREPARATION OF BIS(AMIDOCARBOXYLIC ACIDS)

[75] Inventors: Janet L. Coope, Cliffside Park; AnneMarie Brescia, Fairview, both of N.J.; Stephen A. Madison, New City, N.Y.

[73] Assignee: Lever Brothers Company, Division of Conopco, Inc., New York, N.Y.

[21] Appl. No.: 152,041

[22] Filed: Nov. 12, 1993

[51] Int. Cl.$^6$ .................. C07C 229/04; C07C 229/34
[52] U.S. Cl. .................................................. 562/450
[58] Field of Search ........................................ 562/450

[56] References Cited

U.S. PATENT DOCUMENTS

| | | | |
|---|---|---|---|
| 4,634,551 | 1/1987 | Burns et al. | 252/102 |
| 4,686,063 | 8/1987 | Burns | 252/102 |
| 5,061,807 | 10/1991 | Gethoffer et al. | 548/473 |
| 5,098,598 | 3/1992 | Sankey et al. | 252/186.42 |
| 5,132,431 | 7/1992 | Fuchs et al. | 548/473 |
| 5,268,003 | 12/1993 | Coope et al. | 252/95 |

FOREIGN PATENT DOCUMENTS 949568  7/1953  Germany .
159285  4/1987  Indonesia .

WO90/14336  11/1990  WIPO .

OTHER PUBLICATIONS

J. Prakt. Chem 17, 147–153 (1962).
Cekuoliene, Liet. TSR Mokslu Akad. Darb. Ser. B, (6) 105–9 (1973) *Abstract*.

*Primary Examiner*—José G. Dees
*Assistant Examiner*—Joseph M. Conrad, III
*Attorney, Agent, or Firm*—Milton L. Honig

[57] ABSTRACT

A process is reported for the preparation of bis-(amidocarboxylic acid) involving the steps of:

(i) charging a reactor with an acyl halide and an aminocarboxylate compound being formed from and selected from lactams and aminocarboxylic acids;

(ii) slowly adding to the reaction medium an alkali at a rate to maintain a pH between 10 and 14; and (iii) recovering the bis(amidocarboxylic acid) from the reaction medium.

The recovery procedure advantageously includes acidification of the reaction medium to a pH between 4.5 and 7. The preferred product of the process is N,N'-terephthaloyl-di(6-aminocaproic acid).

7 Claims, No Drawings

PROCESS FOR THE PREPARATION OF BIS(AMIDOCARBOXYLIC ACIDS)

BACKGROUND OF THE INVENTION

1. Field of the Invention

The invention relates to a process for preparing bis(amidocarboxylic acids) which are key intermediates in the synthesis of bis(amidoperoxycarboxylic acid) bleaches.

2. Related Art

Peroxyacids have long been known for their excellent fabric bleaching activity. More recently, amido peroxycarboxylic acids have been identified as particularly desirable because of their good stability in detergent compositions.

U.S. Pat. No 4,634,551 (Burns et al) and U.S. Pat. No. 4,686,063 (Burns) describe peroxyacids having polar amide links along a hydrophobic backbone. All of the reported substances are monoperoxycarboxylic acids. U.S. Pat. No. 5,061,807 (Gethoffer et al) and U.S. Pat. No. 5,132,431 (Fuchs et al) describe a series of imido peroxyacids, chief among which is N-phthaloylaminoperoxycaproic acid (PAP). See also the related technology in EP 0 347 724 (Ausimont).

Bis(amidoperoxy acids) have been disclosed in WO 90/14336 (Interox) which especially describes N,N'-terephthaloyl-di(6-aminoperoxycaproic acid), known as TPCAP. The exceptional stability of TPCAP, and related compounds, have occasioned the need for an improved synthesis. Especially necessary is a route to the intermediate N,N'-terephthaloyl-di(6-aminocaproic acid) known as TOCAP.

The literature has described various syntheses for TOCAP and related compounds. German Patent 949,568 (Kruckenberg) describes the reaction of caprolactam with various acyl halides including adipoyl dichloride in the presence of sodium hydroxide. Once sodium 6-aminocaproate has formed, the reactor is charged with a first portion acyl halide, sodium hydroxide and then a final portion acyl halide. Example 1 best details this process. Synthesis of TOCAP is reported by Zinner et al in *J. Prakt. Chem.* 17, 147–153 (1962). The procedure requires the addition of all the sodium hydroxide to be charged to the reaction vessel at the beginning of the synthesis. The reported yield is 70% of theory. Plate-like crystals are recovered through recrystallization from dimethyl formamide/water (2:5).

The problem with the aforementioned synthetic routes is that the yields are insufficiently high for commercial purposes. Secondly, these syntheses result in substantial amounts of undesirable by-products, especially the monoamide addition by-product. These by-products can lead to thermal instability and impact sensitivity in any eventual peracid formed therefrom.

Accordingly, it is an object of the present invention to provide an improved synthesis of bis(amidocarboxylic acids).

A more specific object of the present invention is to provide a route to bis(amidocarboxylic acids) that achieves high yields.

A further specific object of the present invention is to provide a route to bis(amidocarboxylic acid) in which undesirable by-products are minimized.

A still further object of the present invention is to provide a route to bis(amidocarboxylic acid) through an environmentally friendly procedure wherein product cleanly and with minimal workup separates from the reaction medium.

These and other objects of the present invention will become more readily apparent through consideration of the following summary, detailed description and examples.

SUMMARY OF THE INVENTION

A process is provided for the preparation of a bis(amidocarboxylic acid) having the formula:

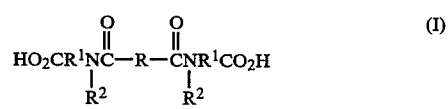

wherein

R and $R^1$ are each a $C_1$-$C_{12}$ radical independently selected from the group consisting of alkylene, alkenylene, cycloalkylene, cycloalkenylene, arylene and phenylene radicals; and $R^2$ is hydrogen or a $C_1$-$C_{12}$ radical selected from the group consisting of alkyl, alkenyl, cycloalkyl, cycloalkenyl, aryl and phenylene radicals;

the process comprising the steps of:

(i) charging a reactor with a reaction medium that includes an acyl halide and an aminocarboxylate compound, the acyl halide having the formula:

the aminocarboxylate compound being formed from and selected from the group consisting of lactams having the formula:

and aminocarboxylic acids having the formula:

(ii) slowly adding to the reaction medium an alkali at a rate to maintain a pH between 10 and 14; and (iii) recovering the bis(amidocarboxylic acid) from the reaction medium.

DETAILED DESCRIPTION

Now it has been found that bis(amidocarboxylic acid) can be prepared in high yield and purity by slow addition of alkali at a pH maintained between 10 and 14, preferably between 11 and 12, to a reaction mixture of a corresponding acyl halide and an aminocarboxylate compound.

Accordingly, in its broadest aspect, the invention provides a process for the preparation of bis(amidocarboxylic acid) having the formula:

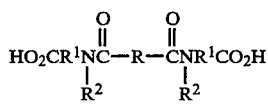

wherein

R and $R^1$ are each a $C_1$-$C_{12}$ radical independently selected from the group consisting of alkylene, alkenylene, cycloalkylene, cycloalkenylene, arylene and phenylene radicals; and $R^2$ is hydrogen or a $C_1$-$C_{12}$ radical selected from the group consisting of alkyl, alkenyl, cycloalkyl, cycloalkenyl, aryl and phenylene radicals.

There are two key reactants to the process of this invention. The first is an acyl halide having the formula:

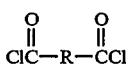

The following acyl halides are representative of the present invention.

| | |
|---|---|
| terephthaloyl chloride | sebacoyl chloride |
| phthalyl chloride | suberoyl chloride |
| succinoyl dichloride | trans-1,4-cyclohexanedicarbonyl dichloride |
| adipoyl dichloride | trans-1,2-cyclobutanedicarbonyl dichloride |
| dodecanedioyl dichloride | |

The most preferred is terephthaloyl chloride.

The second essential reactant of the present invention is that of an aminocarboxylate compound. The compound may be formed from hydrolysis of a lactam (III) or from deprotonation of an aminocarboxylic acid (IV) with an alkali base.

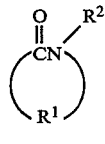

and

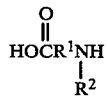

The following aminocarboxylate compounds are representative of the present invention.

| LACTAMS | AMINOCARBOXYLIC ACIDS |
|---|---|
| ε-caprolactam | 6-aminocaproic acid |
| N-methyl caprolactam | 4-aminobenzoic acid |
| δ-valerolactam | 2-aminobenzoic acid |
| α-butyrolactam (2-pyrrolidone) | 3-amino propionic acid |
| | 4-aminobutyric acid |
| | N-methyl-6-amino hexanoic acid |
| | N-ethyl-3-aminopropionic acid |
| | N-methyl-4-aminobenzoic acid |
| | 4-amino-cyclohexanoic acid |
| | glycine |
| | alanine |
| | valine |
| | leucine |
| | phenyl alanine |

| LACTAMS | AMINOCARBOXYLIC ACIDS |
|---|---|
| | lysine |

The molar amount of acyl halide relative to aminocarboxylate compound will range from about 1:4 to about 1:2, preferably about 1:2.

The alkali is a base which may be selected from the group consisting of sodium hydroxide, lithium hydroxide, calcium hydroxide, magnesium hydroxide, potassium hydroxide, sodium carbonate, potassium carbonate and sodium methoxide. Most preferred is sodium hydroxide which may be employed in concentrations of 10–50% in water. The molar amount of alkali relative to the acyl halide will be in an amount from about 3:1 to about 1:1, preferably about 2:1.

According to the process of the present invention, a reactor is charged with a reaction medium that includes the acyl halide and the aminocarboxylate compound. Solvent may also be present. Suitable solvents include water, alcohols such as methanol, halocarbons such as methylene chloride, hydrocarbons such as pentane, aromatics such as toluene, and ethers. Most preferred is water.

Crucial for the process is the slow introduction of the alkali to the reaction medium at a rate to maintain a pH between 10 and 14.

Temperatures of the reaction may range from about 0° C. to about 100° C., but preferably between about 10° C. and 40° C., optimally about 15° C.

Subsequent to the reaction, the bis(amidocarboxylic acid) (I) can be recovered by selective precipitation. In a further aspect of the present invention, it has been noted in connection with TOCAP that the pH for workup advantageously should not be lower than 4.5, preferably ranging between 5.0 and 7.0, optimally between about 5.5 and 6.5.

The following Examples will more fully illustrate the embodiments of this invention. All parts, percentages and proportions referred to herein and in the appended claims are by weight unless otherwise noted.

EXAMPLE 1

Mettler DL70 Titrator

A Mettler DL70 Titrator equipped with a mechanical stirrer and a pH sensor (DG111-SC) was used for the pH control reactions. The pH electrode was calibrated using Fisher pH buffers. Sodium hydroxide was titrated in from a 20 mL burette. Accuracy of pH control was ±0.01. The jacketed reaction vessel was cooled by a Neslab RTE-100 refrigerated circulating bath; temperature control ±0.1° C.

Mettler DL70 Titrator Procedure

A jacketed 100 mL titration vessel was maintained at 15° C. by a circulating cooling bath. 6-Aminocaproic acid (10.416 g, 0.0794 mol, 2.1 equiv.) was dissolved in 20 mL of 14% aqueous NaOH (0.0794 mol, 2.1 equiv.) at 25° C. to form a solution of sodium 6-aminocaproate. The solution was placed into a 100 mL jacketed beaker which was maintained at 15° C. by a circulating cooling bath. Terephthaloyl chloride (7.674 g, 0.0378 mol, 1 equiv) was added in one portion and the reaction mixture stirred rapidly with a mechanical stirrer. The original pH of the solution was 12.8. As hydrochloric add was generated by the condensation of terephthaloyl chloride and sodium 6-aminocaproate, the pH began to fall. When the pH electrode in the solution sensed that the pH had dropped below the specified pH (in this case, pH=11.00), 14% NaOH was automatically titrated into the reaction to neutralize the hydrochloric acid. In this way the desired pH was maintained for the duration of the reaction. Completion of the reaction can be monitored visually by noting the disappearance of solid terephthaloyl chloride, or by uptake of sodium hydroxide with respect to the required theoretical amount. At the end of the reaction, the mixture was filtered through a bed of celite on a Buchner funnel to remove any unreacted terephthaloyl chloride. The product was precipitated by addition of 2.1 equivalents of 1 molar aqueous sulfuric acid isolated by filtration. The resulting white solid was washed with water to remove any residual NaCl, $Na_2SO_4$ or 6-aminocaproic acid. Typical yields: 90-93%.

Analysis

Melting point: 214°-217° C.
1H NMR (200 mHz, DMSO-$d_6$) δ 8.57 (t,2H), 7.91 (s, 4H), 3.25 (q, 4H), 2.22 (t, 4H), 1.57-1.32 (m,12H).
Terephthalic acid appears at 8.05, monoaddition by-product appears at 8.68 (t, NH) and 7.95-8.07 (q). 13C NMR (300 mHz, DMSO-$d_6$) δ 166.93, 157.96, 129.24, 119.53, 26.09, 21.28, 18.53, 16.74. Monoaddition impurity is visible at δ 121.67.

Mass Spectroscopy, low resolution (CI, isobutane) 421.2 (MH+, methyl ester). Monoaddition impurity is invisible at 308.1 (MH+, methyl ester).

IR (nujol)3320 (NH), 1720, 1705, 1630, 1545, 1475, 1350, 1320, 1300, 1285, 1235, 1160, 1105, 1020, 950, 870, 860, 740, 730 $cm^{-1}$.

HPLC

Mobile phase was 18:82 acetonitrile: water; 1.7 g/l tetrabutylammonium hydrogen sulfate, pH adjusted to 8 with triethylamine; Flow rate: 1.5 mL/min; Column: Hamilton PRP-1; UV Detection-230 nm.

Retention times: 7.85 rain (product), 5.35 min (monoaddition), 4.15 min (terephthalic acid).

EXAMPLE 2

ε-Caprolactam as a Starting Material

Caprolactam (0.0894 mol, 2.1 equiv.) was refluxed in 20 mL of about 14% sodium hydroxide (0.0894 mol, 2.1 equiv.). After refluxing for two hours, the reaction mixture was cooled and transferred to the 100 mL jacketed autotitrator vessel which was maintained at 15° C. by a circulating bath. One equivalent of terephthaloyl chloride flakes (8.64 g, 0.0426 mol) was added and the reaction was maintained at pH 11.2 by titration of NaOH solution. After three hours, the reaction solution was filtered; unreacted acid chloride amounted to 7.4% of the acid chloride used. The product was precipitated with sulfuric acid and washed with water. An 87% yield was realized with purity of 93.9% TOCAP diacid, 2.2% monoaddition and 0.6% terephthalic acid.

EXAMPLE 3

A series of pH stat experiments were conducted using the Mettler DL70 Titrator as described in Example 1. Table I lists the results of the reactions conducted using the autotitrator.

TABLE I

Results of Autotitrator Experiments

| Run | pH | RXN Time (Hours) | NaOH Used (% of Theory) | Yield (%) | % Purity by HPLC[1] TOCAP | Mono Amide[2] |
|---|---|---|---|---|---|---|
| 1 | 9.00 | 5 | 57 | 57 | 93.7 | 2.1 |
| 2 | 10.00 | 4.25 | 86 | 90 | 95.6 | 1.1 |
| 3 | 11.00 | 3 | 93 | 91 | 96.4 | 0.6 |
| 4 | 11.17 | 3 | 88 | 91 | 97.0 | 0.7 |
| 5 | 12.00 | 1 | 100 | 93 | 98.2 | 0.7 |
| 6 | 13.00 | 1 | — | 95 | 96.5 | 1.0 |

[1]Estimated error in calculations is ±0.05%
[2]N-(4-carboxybenzoyl)-6-aminocaproic acid Reactions were monitored by the uptake of sodium hydroxide. The theoretical amount of sodium hydroxide needed to neutralize two moles of hydrochloric acid per mole of terephthaloyl chloride was calculated and the percent of this theoretical amount actually consumed by the reaction recorded. Reactions were also stopped when no acid chloride was visible in the reaction vessel, or, as in runs 1 and 2, when the reaction proceeded very slowly and the uptake of sodium hydroxide had slowed to a minimum. The highest purities were attained from reactions controlled between pH 11.00 and 12.00 and maintained at a temperature of 15° C. (runs 3-5). Although comparable purities were obtained, the reaction proceeded to completion in one hour when conducted at pH 12.00 as opposed to three hours at pH 11.00. Lower pH's (runs 1 and 2)led to longer reaction times and lower purities.

EXAMPLE 4

The product workup outlined in Example 1 was investigated with respect to varying pH. Table II reports the relationship of pH in the workup slurry to the purity of TOCAP product. Yield of TOCAP in all the workups remained constant at 62-64%.

TABLE II

Comparison of Purities with Respect to Slurry pH

| Workup | pH of Slurry | HPLC ANALYSIS TOCAP (%) | Mono Amide (%) | Terephthalic Acid (%) |
|---|---|---|---|---|
| 1 | 3.2 | 76 | 14.7 | 3.6 |
| 2 | 4.1 | 78.1 | 14.4 | 3.3 |
| 3 | 5.2 | 84.4 | 9.3 | 0.1 |
| 4 | 6.1 | 92.3 | 2.7 | 0.05 |

Purities of product resulting from the final slurry pH of a very impure sample derived from the Zinner procedure run at ambient temperature is shown in Table II. As workup pH increases from 3.2 to 6.1, the amount of terephthalic acid starting material (hydrolyzed acyl chloride) decreases. Likewise, the amount of monoamide by-product which precipates from solution also decreases. Highest purity is thus isolated at pH 6.1. As pH decreases, the purity decreases. Optimum purity is found in the region of pH 5 to pH 6.5. Any pH higher than 7 results in a forfeiture of yield.

The foregoing description and Examples illustrate selected embodiments of the present invention. In light thereof, various modifications will be suggested to one skilled in the art, all of which are in the spirit and purview of this invention.

What is claimed is:

1. A process for the preparation of a bis(amidocarboxylic acid) having the formula:

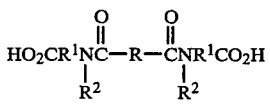 (I)

wherein

R and $R^1$ are each a $C_1$-$C_{12}$ radical independently selected from the group consisting of alkylene, alkenylene, cycloalkylene, cycloalkenylene, arylene and phenylene radicals; and $R^2$ is hydrogen or a $C_1$-$C_{12}$ radical selected from the group consisting of alkyl, alkenyl, cycloalkyl, cycloalkenyl, aryl and phenylene radicals;

the process comprising the steps of:

(i) charging a reactor with a reaction medium that includes an acyl halide and an aminocarboxylate compound, the acyl halide having the formula:

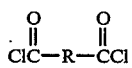 (II)

the aminocarboxylate compound being formed from and selected from the group consisting of lactams having the formula:

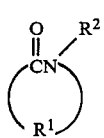 (III)

and aminocarboxylic acids having the formula:

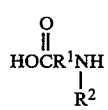 (IV)

(ii) allowing the acyl halide and aminocarboxylate compound to react and during the reacting slowly adding to the reaction medium an alkali at a rate to maintain a pH between 10 and 14; and (iii) recovering the bis(amidocarboxylic acid) from the reaction medium.

2. A process according to claim 1 wherein the alkali is selected from the group consisting of sodium hydroxide, lithium hydroxide, calcium hydroxide, magnesium hydroxide, sodium carbonate, potassium hydroxide, potassium carbonate and sodium methoxide.

3. A process according to claim 1 wherein the acyl halide is N,N'-terephthaloyl chloride.

4. A process according to claim 3 wherein the lactam is ε-caprolactam.

5. A process according to claim 3 wherein the aminocarboxylic acid is 6-aminocaproic acid.

6. A process according to claim 1 wherein step (iii) includes precipitating from the reaction medium the bis(amidocarboxylic acid) at a pH between 4.5 and 7.

7. A process according to claim 1 wherein the bis(amidocarboxylic acid) is N,N'-terephthaloyl-di(6-aminocaproic acid).

* * * * *